United States Patent
Bruegger (10) Patent No.: US 6,699,718 B1
(45) Date of Patent: Mar. 2, 2004

(54) METHOD, REAGENT AND TEST CARTRIDGE FOR DETERMINING CLOTTING TIME

(75) Inventor: Berndt B. Bruegger, Camarillo, CA (US)

(73) Assignee: Roche Diagnostics Corporation, Indianapolis, IN (US)

( * ) Notice: Subject to any disclaimer, the term of this patent is extended or adjusted under 35 U.S.C. 154(b) by 361 days.

(21) Appl. No.: 09/645,786

(22) Filed: Aug. 24, 2000

Related U.S. Application Data (60) Provisional application No. 60/152,450, filed on Sep. 3, 1999.

(51) Int. Cl.[7] ............................................. G01N 33/86
(52) U.S. Cl. ........................ 436/69; 436/8; 436/18; 422/73; 73/64.41; 600/369; 435/113
(58) Field of Search ................................ 436/63, 69, 8, 436/17, 18, 180; 422/58, 59, 73, 100; 73/64.41; 600/368, 369; 252/408.1; 435/13

(56) References Cited

U.S. PATENT DOCUMENTS

| | | | |
|---|---|---|---|
| 4,666,831 A | 5/1987 | Janoff et al. | |
| 4,672,030 A | 6/1987 | Witt | |
| 4,732,860 A | 3/1988 | Bartl et al. | 436/34 |

(List continued on next page.)

FOREIGN PATENT DOCUMENTS

| | | |
|---|---|---|
| CA | 1250213 | 2/1989 |
| CA | 2096212 | 5/1993 |
| EP | 0 123 883 | 11/1984 |
| EP | 0 394 070 | 10/1990 |
| EP | 0 570 356 | 11/1993 |
| WO | WO 96/15457 | 5/1996 |
| WO | PCT/US00/23249 | 8/2000 |

OTHER PUBLICATIONS

Bach, R. R. "Initiation of Coagulation By Tissue Factor"; *CRC Critical Reviews in Biochemistry*; 1988, vol. 23, No. 4, pp. 339–368.

Gailani, D.; Broze, Jr., G. J. "Factor XII–Independent Activation of Factor IX in Plasma: Effects of Sulfatides on Tissue Factor–Induced Coagulation"; *Blood*; 1993, vol. 82, No. 3, pp. 813–819.

Gomperts, E. D.; Zucker, M. L. "Heparin, Brain Thromboplastin and the Insensitivity of the Prothrombin Time to Heparin Activity"; *Thrombosis Research*; 1977, vol. 12, pp. 105–117.

Hattersley, P. G. "Activated Coagulation Time of Whole Blood"; *JAMA*; 1966, vol. 196, No. 5, pp. 150–154.

Kyogashima, M.; Onaya, J.; Hara, A.; Taketomi, T. "Contradictory Functions of Sulfatide in the Blood Coagulation System as Coagulant and Anticoagulant", *Acta Biochimica Polonica*; 1998, vol. 45, No. 2, pp. 493–499.

Kyogashima, M.; Onaya, J.; Hara, A.; Taketomi, T. "Sulfatide Can Markedly Enhance Thrombogenesis in Rat Deep Vein Thrombosis Model"; *Glyconjugate Journal*; 1998, vol. 15, pp. 915–922.

*Primary Examiner*—Maureen M. Wallenhorst
(74) *Attorney, Agent, or Firm*—Brinks Hofer Gilson & Lione (57) ABSTRACT

The invention is a method, reagent and test cartridge for the determination of the clotting time of a blood sample by means of a reagent containing tissue factor and a sulfatide. In an alternative embodiment, the reagent may contain tissue factor and at least one of the group consisting of a phosphatide and a sulfatide. This invention is preferably used to monitor the effectiveness of heparin therapy in patients that have been administered low to moderate heparin doses to achieve blood heparin levels from 0 to about 3 U/mL, and may also be used for determining clotting time at higher heparin levels of up to about 6 U/mL.

26 Claims, 3 Drawing Sheets

U.S. PATENT DOCUMENTS

| | | | |
|---|---|---|---|
| 4,755,461 A | | 7/1988 | Lawson et al. |
| 4,756,884 A | | 7/1988 | Hillman et al. |
| 4,946,775 A | | 8/1990 | Yin |
| 5,039,617 A | | 8/1991 | McDonald et al. |
| 5,300,779 A | | 4/1994 | Hillman et al. |
| 5,314,695 A | * | 5/1994 | Brown .................... 424/450 |
| 5,401,663 A | | 3/1995 | Yonemura |
| 5,443,959 A | | 8/1995 | Kikuchi et al. |
| 5,472,852 A | | 12/1995 | Smirnov et al. |
| 5,506,112 A | | 4/1996 | Lang et al. |
| 5,512,304 A | | 4/1996 | Barrow et al. |
| 5,550,028 A | | 8/1996 | Lee et al. |
| 5,625,036 A | * | 4/1997 | Hawkins et al. ........... 530/381 |
| 5,705,395 A | | 1/1998 | Griffin et al. |
| 5,770,699 A | | 6/1998 | King |
| 5,834,223 A | | 11/1998 | Griffin et al. |
| 6,083,757 A | * | 7/2000 | Griffin et al. ................. 436/69 |
| 6,100,072 A | * | 8/2000 | Brucato et al. ............ 435/69.7 |
| 6,183,979 B1 | * | 2/2001 | Lee et al. ..................... 435/13 |

OTHER PUBLICATIONS

Lehninger; *Biochemistry*, $2^{nd}$ *Edition*; Worth Publishers, New York, 1975, pp. 287–291.

Mungall, D. R.; Wright, J. "Summary Report: Performance Evaluation of the CoaguChek™Plus Coagulation System for Determination of the Prothrombin Time Test"; 1995, Boehringer Mannheim Corporation, Indianapolis, pp. 1–8.

Naito, K.; Fujikawa, K. "Activation of Human Blood Coagulation Factor XI Independent of Factor XII"; *The Journal of Biological Chemistry*; 1991, vol. 266, No. 12, pp. 7353–7358.

Paborsky, L. R.; Tate, K. M.; Harris, R. J.; Yansura, D. G.; Band, L.; McCray, G.; Gorman, C. M.; O'Brien, D. P.; Chang, J. Y.; Swartz, J. R.; Fung, V.P.; Thomas, J. N.; Vehar, G. A. "Purification of Recombinant Human Tissue Factor"; *Biochemistry*; 1989, vol. 28, No. 20, pp. 8072–8077.

Rehemtulla, A.; Pepe, M.; Edgington, T.S. "High Level Expression of Recombinant Human Tissue Factor in Chinese Hamster Ovary Cells as a Human Thromboplastin"; *Thrombosis and Haemostasis*; 1991, vol. 65, No. 5, pp. 521–527.

Schousboe, I; Rasmussen, M. S. "The Effect of $\beta_2$–Glycoprotein I on the Dextran Sulfate and Sulfatide Activation of the Contact System (Hageman Factor System) in the Blood Coagulation"; *Int. J. Biochem.*; 1988, vol. 20, No. 8, pp. 787–792.

Scott, C. F.; Colman, R. W. "Fibrinogen Blocks the Autoactivation and Thrombin–Mediated Activation of Factor XI on Dextran Sulfate"; *Proc. Natl. Acad. Sci. USA*; Biochemistry; 1992, vol. 89, pp. 11189–11193.

Shimada, T.; Sugo, T.; Kato, H.; Yoshida, K.; Iwanaga, S. "Activation of Factor XII and Prekallikrein with Polysaccharide Sulfates and Sulfatides: Comparison with Kaolin–Mediated Activation"; *J. Biochem*; 1985, vol. 97, No. 2, pp. 429–439.

Tans, G.; Griffin, J. H. "Properties of Sulfatides in Factor–XII–Dependent Contact Activation"; *Blood*; 1982, vol. 59, No. 1, pp. 69–75.

Tans, G.; Rosing, J.; Griffin, J. H. "Sulfatide–Dependent Autoactivation of Human Blood Coagulation Factor XII (Hageman Factor)"; *The Journal of Biological Chemistry*, 1983, vol. 258, No. 13, pp. 8215–8222.

Tans, G.; Griffin, J. H. "Initiation of Contact Activation by Sulfatides"; *Adv. Exp. Med. Biol.*, 1983, vol. 156, pp. 63–72.

Tans, G.; Verkleij, A. J.; Yu, J.; Griffin, J. H. "Sulfatide Bilayers as a Surface for Contact Activation in Human Plasma"; *Biochemical and Biophysical Research Communications*; 1987, vol. 149, No. 3, pp. 1002–1007.

Abstract of: Aiyappa, P. A. "Chromogenic Substrate Spectrophotometric Assays for the Measurement of Clotting Function"; *Ann. N. Y. Acad. Sci.*; 1981, vol. 370, 812–821.

Abstract of: Bader, R.; Mannucci, P. M.; Tripodi, A.; Hirsh, J.; Keller, F.; Solleder, E. M.; Hawkins, P.; Peng, M.; Pelzer, H.; Teijidor, L.M. et al. "Multicentric Evaluation of a New PT Reagent Based on Recombinant Human Tissue Factor and Synthetic Phospholipids"; *Thromb. Haemost.*; 1994, vol. 71, No. 3, pp. 292–299.

Abstract of: Hara, A.; Kutsukake, Y.; Uemura, K.I.; Taketomi, T. "Anticoagulant Activity of Sulfatide and its Anti–Thrombotic Effect in Rabbit"; *J. Biochem. (Tokyo)*; 1993, vol. 113, No. 6, pp. 781–785.

Abstract of: Sakai, T.; Kisiel, W. "Formation of Tissue Factor Activity Following Incubation of Recombinant Human Tissue Factor Apoprotein with Plasma Lipoproteins"; *Thromb. Res.*; 1990, vol. 60, No. 3, pp. 213–222.

Abstract of: Scarpati, E. M.; Wen, D.; Broze, Jr., G. J.; Miletich, J. P.; Flandermeyer, R. R.; Siegel, N. R.; Sadler, J. E. "Human Tissue Factor: cDNA Sequence and Chromosome Localization of the Gene"; *Biochemistry*; 1987, vol. 26, No. 17, pp. 5234–5238.

"PT Test Cartridges"; Package Insert, Mannheim Boehringer Corporation, 1994.

"APTT Test Cartridges"; Package Insert, Mannheim Boehringer Corporation, 1994.

"Activated THROMBOFAX® Reagent–Optimized", Package Insert, Hemoliance.

Abstract of: JP Patent No. 10072355 A; "Influenza Virus Adsorption Inhibitor"; assigned to Snow Brand Milk Prod. Co. Ltd., Suzuki T (Suzu–I), and Suzuki Y (Suzu–I).

Abstract of: JP Patent No. 62283934 A; "Liposome Prepn. Contg. Interferon"; assigned to Vitamin Kenkyusho K (Vita–N).

Abstract of: EP Patent No. 226370 A; "Adriamycin Entrapping Liposome Prepn. For Improved Antitumor Use"; assigned to Inst. App. Biochem. (Bioc–N), Oyo Seikagaku Kenyusho KK (Oyos–N), and Vitamin Kenkyusyo KK (Vita–N).

* cited by examiner

FIG. 4A
Evaluation of Sample Temperature Effects on the PRO LR ACT Assay
Assayed LR ACT cartridge production lot ACT021898
Center line is the mean of all assay values with the 2.S.D. range shown by lines above and below the mean.
Also see Figures 4B and 4C.

FIG. 4B
Blood Heparin Level Adjusted to 1.5 U/mL

FIG. 4C
Blood Heparin Levels Adjusted to 3.0 U/mL

METHOD, REAGENT AND TEST CARTRIDGE FOR DETERMINING CLOTTING TIME

This application claim priority to provisional application serial No. 60/152,450, filed Sep. 3, 1999.

BACKGROUND OF THE INVENTION

The present invention relates to the field of determining the clotting time of blood samples and more specifically relates to the determination of the clotting time of blood samples from patients receiving heparin treatment, particularly patients that have been administered low to moderate heparin doses, as well as that of patients that have been administered high heparin doses.

The activated clotting time (ACT) assay is a blood test that monitors the effectiveness of heparin dosing. The levels of heparin that the ACT assay is monitoring are generally beyond the range of the activated partial thromboplastin time (APTT) assay. Some APTT assays can monitor plasma heparin levels as high as 1.5 U/mL (which is equivalent to a blood heparin level of about 0.75 U/mL), while the ACT assay can monitor blood heparin levels generally as high as 6 U/mL. The higher end of the blood heparin range (high range; HR) is often used in cardiac pulmonary bypass surgery, while blood levels under 3 U/mL (moderate to low range; LR) but above the effective range of the APTT assay, are used in situations such as cardiac catheterization, extracorporeal membrane oxygenation (ECMO), hemodialysis, and percutaneous transluminal coronary angioplasty (PTCA).

There are various commercially available ACT assays. These typically differ in the specific component that activates clotting, which difference can affect the blood heparin range in which the assay is reliable. Consequently, these assay types are often categorized by the heparin range and corresponding surgical or medical application. One example of such a test is known as the Hemochron® sold by International Technidyne Corporation. The basic procedure for this test is as follows: A two mL sample of blood is added to a test tube containing dried celite (diatomaceous earth) and a small magnetic bar. The test tube is capped and shaken, then placed in an instrument that starts spinning of the magnetic bar. When the blood begins to clot, the magnetic bar slows or stops spinning. The instrument then notes the length of time till the magnet stopped spinning as the celite ACT time. A variation of this test is known as the Hemochron® glass ACT assay wherein the test tube is plastic and contains glass particles with a magnetic bar and the sample is only 0.4 mL of blood.

U.S. Pat. No. 4,756,884 and 5,039,617 describe an integrated device containing a predispensed, dry reagent in a capillary track that can be used to measure clotting of blood samples. The entire disclosure of these two patents is incorporated herein by reference. The assignee of the present invention currently markets a system under the designation CoaguChek™ Pro and CoaguChek™ Plus. Certain challenges were presented in designing a reagent for use in this system to measure heparin effectiveness in the range of 3 U/mL and lower. For example, the CoaguChek™ Plus/Pro system should have an assay time of 300 seconds or less, whereas traditional ACT reagents have an assay time of up to 1000 seconds.

In addition, the activators that have been traditionally used in ACT reagents are celite, kaolin or glass particles, which are all insoluble particles. Such activators are typically problematic for the cartridge-reagent system employed in the CoaguChek™ Plus system which uses the blood sample to solubilize the reagent and move the reagent with the blood through the cartridge tracks during the coagulation activation reaction.

SUMMARY OF THE INVENTION

Briefly stated, the invention is a method, reagent and test cartridge for the determination of the clotting time of a blood sample by means of a reagent comprising tissue factor and a co-factor. A preferred co-factor is a sulfatide. This invention is preferably used to monitor the effectiveness of heparin therapy in patients that have been administered low to moderate heparin doses that result in blood heparin levels from about 0 to about 3 U/mL. However, it has been surprisingly discovered that the invention can monitor the effectiveness of heparin therapy in patients that have been administered higher heparin doses resulting in blood heparin levels of up to about 6 U/mL. In an alternative embodiment, the sulfatide may be combined with or replaced by a phosphatide.

In accordance with the test cartridge aspect of the invention, the cartridge includes a housing containing an inlet port, a chamber unit and an exit port. The cartridge preferably further comprises a first capillary unit for independently pumping a liquid, such as a blood sample, from said inlet port to said chamber unit. In addition, the preferred cartridge preferably includes a second capillary unit positioned between and operatively connected to said chamber unit and said exit port for independently pumping a liquid from said chamber unit to said exit port. The inlet port, first capillary unit (if present), chamber unit, second capillary unit (if present), and exit port are present in a continuous capillary pathway. Contained within the capillary pathway are a reagent comprising tissue factor and a co-factor, preferably a sulfatide. In an alternative embodiment, a phosphatide may be combined with a sulfatide or a phosphatide may be the sole co-factor.

It should be noted that, as used herein, the terms thromboplastin, tissue factor, and coagulation factor III are all intended to mean the cell-surface protein that initiates coagulation.

It should also be noted that the term sulfatide refers to a class of sulfate derivatives of cerebrosides, which have the following general structure:

R=fatty acid residue

The term phosphatide refers to a class of glycerol based compounds in which one of the hydroxyl groups is replaced with a phosphoric acid group, and the other hydroxyl groups are replaced with fatty acid esters. Phosphatides are also referred to as phospholipids, phosphoglycerides, and glycerol phosphatides. For more information on phosphatides, see Lehninger, Albert L., *Biochemistry*, $2^{nd}$ Edition, Worth Publishers, NY (1975).

The present invention, together with attendant objects and advantages, may be better understood with reference to the detailed description below in connection with the attached Figures.

DETAILED DESCRIPTION

The invention involves the use of tissue factor (TF) and a co-factor, preferably a sulfatide, in a method, reagent and test cartridge for determining the activated clotting time of a blood sample. In an alternative embodiment, the cofactor may be a phosphatide alone or in combination with a sulfatide.

Tissue factor (TF), also referred to as thromboplastin and clotting factor III, is an integral membrane glycoprotein that functions as an initiator of coagulation. TF and its properties as a biological initiator of this essential hemostatic process are discussed in the review article "Initiation of Coagulation by Tissue Factor", by R. R. Bach, *CRC Crit. Rev. Biochem.* (1988) 23: 339–68.

The tissue factor component of the reagent is preferably recombinant human TF (rHTF). Purification of rHTF has been described in Paborsky et al., *Biochemistry* (1989) 28: 8072–7 and Rehemtulla et al., *Thromb. Haemost.* (1991) 65: 521–7. rHTF used for the reagent of the present invention was purchased from Serbio (catalog No. 77800). Other sources of TF, such as natural extracts of mammalian (human, rabbit, cattle, horse, monkey, etc.) brain, lung, or platelets, etc., can also be used.

Figure 2:
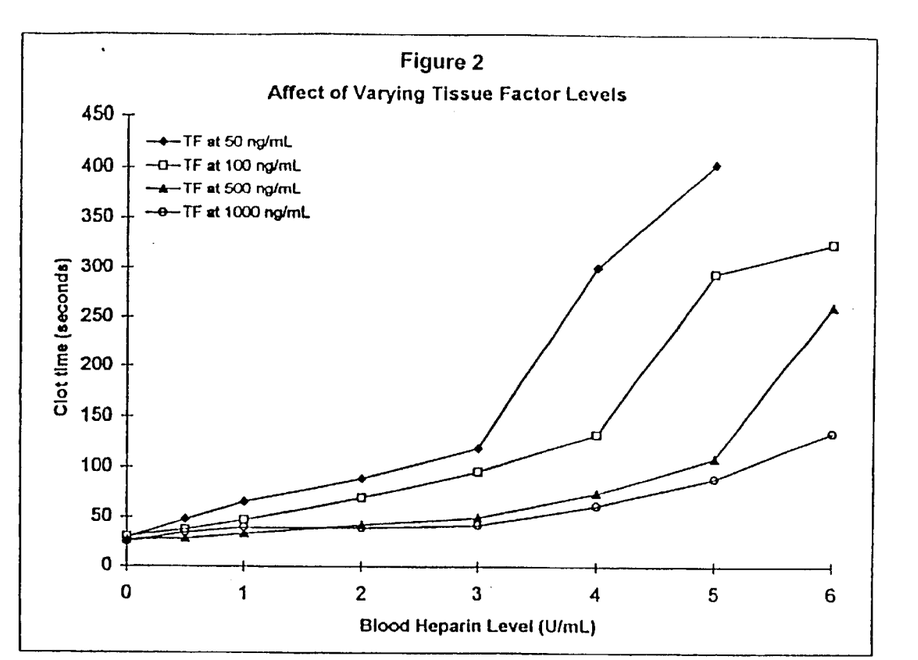
FIG. 2 shows the basic response of heparinized samples to TF-based reagents.

The basic response of heparinized samples to TF-based reagents is shown in FIG. 2. In particular, reagents were formulated as shown in Table 1, with the exception that no added sulfatide or phosphatide was present and the level of TF was varied from 50 ng/mL to 1000 ng/mL. These TF-based reagents were applied to the test cartridges as described above and samples with various heparin levels were tested in them. At high enough levels of tissue factor, the sensitivity of the reagent to heparin is low. As the level of tissue factor drops, sensitivity increases, but with a loss of clot activation with samples containing higher heparin levels.

Figure 3:
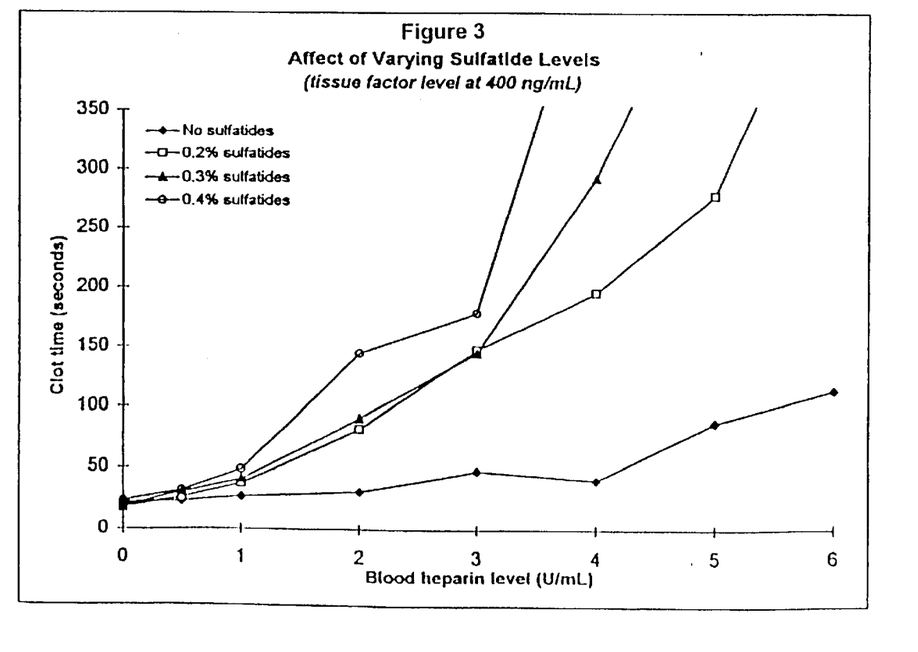
FIG. 3 shows the affect on heparin response of TF-based reagents with varying sulfatide levels.

Co-factors for TF were found that increased the heparin sensitivity in TF-based reagents. For example, sulfatides and phosphatides are co-factors that were found to control the degree of heparin sensitivity elicited by the tissue factor. Nevertheless, phosphatides did not have the consistency in effecting tissue factor heparin sensitivity as that found for sulfatides. FIG. 3 shows the effect on heparin response of varying sulfatide levels combined with 400 ng/mL of TF. In particular, reagents were made according to Table 1 below, with the exception that the TF was present at 400 ng/mL and the sulfatide concentration was varied between 0 and 0.4% of the sample, i.e., between 0 and 4 mg/mL of the sample.

Phosphatides and sulfatides can be combined at optimized ratios and get about the same sensitivity in the assay of the present invention as with sulfatides alone. Phosphatides are more readily available and less costly than sulfatides. Thus, in an alternative embodiment, a combination of sulfatide and phosphatide is utilized wherein the ratio of phosphatide to sulfatide is maximized yet yields optimal sensitivity. Surprisingly, ratios of phosphatide to sulfatide ranging from about 1/3 to about 3/1 by weight were found to have approximately the same sensitivity as sulfatide alone. Heparin levels ranging from about 2 U/mL to about 6 U/mL can be effectively determined using an effective amount of sulfatide, phosphatide, or a combination thereof. Heparin levels ranging from 0 U/mL to about 2 U/mL can be determined using a phosphatide or a phosphatide combined with sulfatide, but it is preferred to use only a sulfatide for this range, or phosphatide combined with sulfatide at a ratio by weight between about 1/3 and about 3/1.

A co-factor, preferably a sulfatide, and in alternative embodiments a phosphatide alone or in combination with a sulfatide, is thus the second important ingredient in the method, reagent and test cartridge. It is to be understood that the term co-factor (or cofactor) as used herein refers to co-factors that can be utilized in combination with TF to determine the effectiveness of moderate to low range, and also preferably high range, heparin dosing in accordance with the present invention, and achieve the desired results in less than about 300 seconds. The term co-factor thus does not include insoluble particles traditionally used as ACT activators, such as celite, kaolin, and glass particles.

Sulfatides, also known as cerebroside sulfates and sulfoglycosylspingolipids, are substances known to be present in mammalian tissues and cell membranes that show procoagulant activity that can be attributed to contact activation reactions. Sulfatides have been studied as intrinsic pathway activators. For a discussion of the properties of sulfatides and their properties as factor-XII dependent contact activation activators, see Tans and Griffin, Blood (1982) 59–69, and Tans et al., *J. Biol. Chem.* (1983) 258: 8215–8222.

A preferred sulfatide for use in the present invention is bovine brain sulfatide purchased from Life Science Research, Inc., or Sigma. A preferred phosphatide for use in the present invention is phosphatidyl choline extracted from soybeans, available from Sigma.

The two reagent components, TF and cofactor (i.e., sulfatide and/or phosphatide), are present in appropriate amounts and proportions in the reagent to achieve the desired results when an effective amount of the reagent is contacted with a sample containing heparin. TF is generally present in an amount in the reagent so that when an effective amount of the reagent is added to a sample (i.e., an amount sufficient to cause clotting in the desired time period), the sample comprises between about 50 and about 1000 ng/mL TF, preferably between about 100 and about 400 ng/mL TF, and most preferably about 100 ng/mL TF. Sulfatide or phosphatide are generally present in an amount in the reagent so that when an effective amount of the reagent is added to a sample, the sample comprises at least about 1 mg/mL of cofactor, and preferably between about 2 and about 4 mg/mL of cofactor, and most preferably about 3 mg/mL of cofactor. If there is a combination of sulfatide and phosphatide, the total concentration of the combination of cofactors present in the sample will be between 2 and 4 mg/mL, and most preferred about 3 mg/mL.

The cofactor (i.e., sulfatide and/or phosphatide) and TF can be precombined in a reagent and used wet in the method of the present invention. This wet reagent is aqueous and preferably provides the levels of TF and co-factor to produce the levels of TF and co-factor in the sample noted above.

Preferably, the TF and sulfatide and/or phosphatide are combined in an aqueous reagent that is dried on the inside surface of a test cartridge, such as that described in U.S. Pat. No. 5,039,617. Preferred methods of making and drying the reagent are described in this same patent. Preferably, the resulting reagent is substantially anhydrous. To facilitate description, the amount of a component in an anhydrous reagent is given as the amount of the component in the aqueous formulation before drying.

In addition to the two essential components TF and a cofactor (preferably a sulfatide and/or a phosphatide), other components can be present in the reagent formulation. For example, bulking additives are preferably used for ease of handling. Preferred bulking agents include sucrose and mannitol and are present at about 40 mg/mL of sample.

A buffer is also preferably included in the reagent. Glycine is currently preferred as the buffer and is present at about 30 mg/mL of sample. Other suitable buffers include tris, bicine and HEPES.

A spreading agent is preferably used to facilitate coating the inside surface of the test cartridge. A preferred spreading agent is gelatin, such as porcine skin gelatin, present at about 10 mg/mL of sample.

A surfactant, such as Triton® X-100 is preferably included at about 0.1 mg/mL of sample. Other conventional surfactants can also be used.

Dyes are also preferably added to the formulation so that during the manufacture of the cartridge a quality control check can be carried out to determine whether reagent has been added to the cartridge. Suitable dyes include Sulforhodamine B and Bromophenol blue, present at about 0.2 mg/mL of sample.

A stabilizing agent, such as Bovine Serum Albumin (BSA) or other mammalian albumins, is preferably added at about 10 mg/mL of sample.

Because the reagent is preferably made quickly, and then dried on a cartridge that is sealed in a pouch, no preservatives are needed. Nevertheless, if the reagent is to be stored wet for any length of time, conventional preservatives can be used.

A preferred formulation for the reagent, together with a number of variations, is set forth in Table 1.

TABLE 1

ACT Reagent Formulation*

| Component | Preferred | Exemplary Composition | Alternative Ingredients |
|---|---|---|---|
| Sulfatide | Bovine Sulfatide | 0.3 g/dL | Phosphatide |
| Tissue factor (TF) | Recombinant human tissue factor (rHTF) | 100 ng/mL | Rabbit Brain TF or other mammalian Brain TF |
| Bulking Additive | Sucrose | 5.0 g/dL | Mannitol and other sugars |
| Buffer | Glycine | 4.0 g/dL | Lysine, Alanine, Hydroxyproline |
| Spreading Agent | Porcine Skin Gelatin | 1.0 g/dL | Fish Gelatin, Calf Gelatin, Collagen, Gum Hydroxypropyl Methyl Cellulose |
| Surfactant | Triton ® X-100 | 0.01 g/dL | Tyloxapol, Pluronic L61, other Triton ® surfactants |
| Dye for Cartridge Inspection | Sulforhodamine B | 0.02 g/dL | Bromophenol blue |
| Stabilizing Agent | Bovine Serum Albumin (BSA) | 1.0 g/dL | Other mammalian albumins |

*Concentration in reconstituted reagent applied to test cartridges, i.e. the amount of the ingredient in the sample.

As noted above, in order to eliminate the handling of reagents by the user of the device and to stabilize the reagents, the reagent is preferably supplied within test cartridges, whereby mixing with the reagent occurs in the cartridge. The reagents may be present either diffusively or non-diffusively to the surface of the cartridge, that is, adhered, absorbed, adsorbed or covalently-linked so that the reagent may become dissolved in the fluid or may remain fixed to the surface. Where the reagents are diffusively bound (non-covalently and weakly bound), a variety of situations can be accommodated. One situation is where the liquid front dissolves all of the reagent, so that the liquid front receives a high concentration of the reagent and most of the reaction occurs at the liquid front. A second situation would be with an excess of a reagent of limited solubility. In this situation, the reagent may be present in the liquid medium at a substantially uniform concentration. A third situation is to have a deficiency of a reagent of limited solubility, so that only the early portion of the fluid will have a relatively constant reagent concentration. It is preferred to disperse a liquid containing the dissolved reagents onto the surface of a reagent chamber. The liquid is spread over the chamber surface and dried under low humidity air.

In order to assure the reproducibility of distribution, various techniques may be employed for introducing the reagent into the chamber. Where the cartridge is produced as two parts which fit together, the reagent may be sprayed, painted, introduced into the chamber as a liquid, lyophilized or evaporated, adsorbed, covalently conjugated, or the like. The active reagent may be combined with various stabilizers, excipients, buffers or other additives involved with the reaction.

To enhance mixing, various mechanical or ultrasonic means may be employed to agitate the sample and reagents, where the mixing means may be internal or external. Vibrators, ultrasonic transducers, magnetic rods or other mechanical mixing means, flow disrupters, mixing baffles or barriers, flow directors, or the like, may be employed. The particular manner in which agitation is provided, if provided, will vary widely depending upon the degree of agitation needed, the design of the cartridge, and the like.

The reagent need not be coated or bound to the surface of the cartridge, but may be provided as a soluble sponge or gel or alternatively, absorbed onto an insoluble sponge, membrane, paper (e.g., filter paper) or gel which is introduced into the reaction unit. In this manner the fluid may pass through the foam structure dissolving the reagent so as to form the reaction mixture.

The reagent may be provided in liquid form in microcapsules. The liquid reagent could be released from the microcapsules by applying pressure to the walls of the reaction unit, resulting in breaking of the microcapsules and releasing the liquid reagent.

To carry out the method of the present invention, a blood sample is brought into contact with an effective amount of the reagent described above. The time until a desired or pre-determined degree of clotting is observed in the blood sample is then measured. As noted above, the method is preferably automated in the devices described. Alternatively, the clotting can be observed visually, or by some other technique and the time recorded manually.

The CoaguChek™ Pro ACT test measures both normal and prolonged activated clotting times using fresh venous or arterial blood. The CoaguChek™ Pro ACT test results are automatically displayed in units equivalent to those obtained with a commercially available ACT test.

Figure 1A:
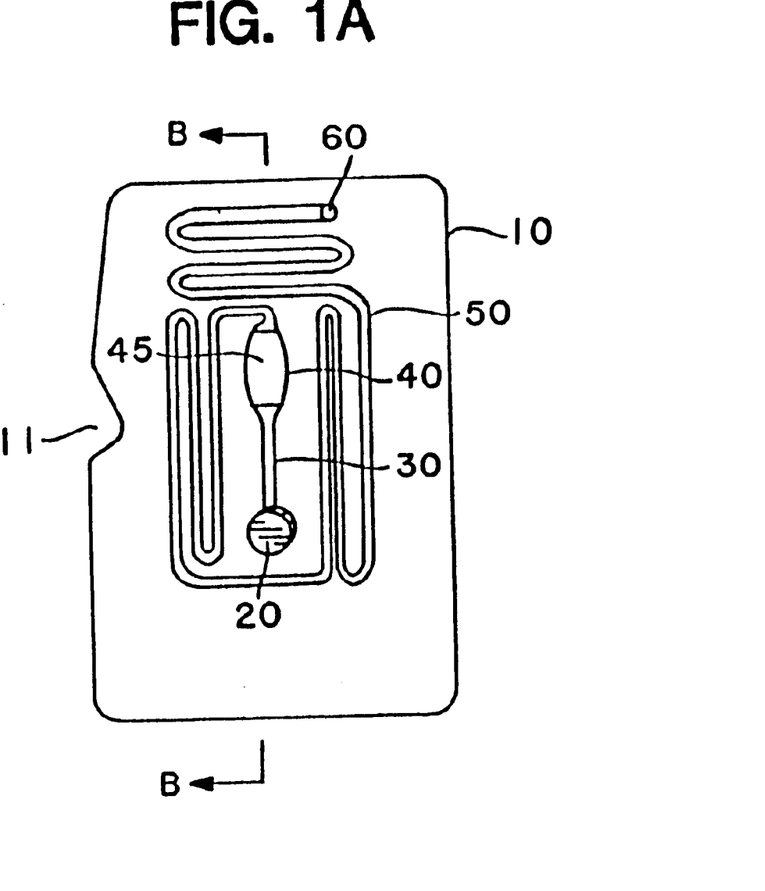
FIGS. 1A and 1B are plan and cross-sectional views of the test cartridge of the present invention.

The preferred test cartridge is shown in FIG. 1A. The device comprises a housing configured so that it may be introduced into an instrument for assay determination. For example, notch 11 in housing 10 is provided to allow retention of the device (e.g., by a spring-activated catch) in the instrument in which the analysis will be carried out. The housing will be constructed so as to ensure sufficient mechanical stability to withstand mechanical handling and provide for the necessary characteristics for flow of the assay medium and detection of the detectable signal. Entry port 20 is provided for access of a blood sample to the internal capillary of the device. A first capillary passage 30 transports blood to reagent chamber 40 containing reagent 45. In the embodiment shown, housing 10 is provided with clear surfaces at the location of capillary 30 in order that this section of the capillary track can be utilized to measure movement (and cession of movement) of blood using a speckle-pattern detector. The blood sample, now mixed with reagent 45, exits chamber 40 and enters capillary flow unit 50, which connects chamber 40 to vent 60. Capillary flow unit 50 is a long, convoluted capillary pathway that provides sufficient path length for flow to be sustained for a time sufficient to measure the activated clotting time (ACT).

Figure 1B:
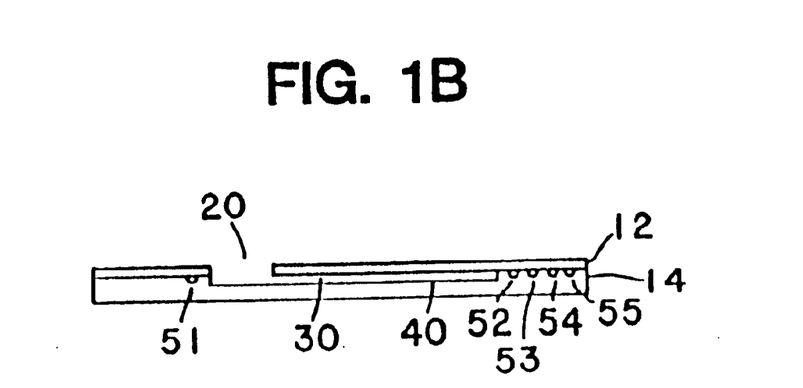

A cross sectional view of the embodiment shown in FIG. 1A is set forth in FIG. 1B. This cross sectional view is taken along the lines B—B of FIG. 1A. The construction of housing 10 from two plates, 12 and 14, is evident in this cross-sectional view. Plate 12 is essentially a flat plate that has been welded onto plate 14, which contains grooves and other depressions in its upper surface that will form the internal chambers and capillaries of the device. The two plastic pieces 12 and 14 have been welded together after being properly aligned (e.g., placed in register). "Registration" is used here in the sense of referring to proper alignment of the depressions present in the surfaces of the two pieces that are used to form the internal chambers and capillaries. Proper registration can be aided by injection molding the two pieces to provide projections on one piece that fit into holes or depressions (other than capillary- or chamber-forming depressions) in the second piece.

A single convoluted depression used to form capillary channels and chambers is present in the surface of plate 12. The cross-sectional view shown in FIG. 1 cuts through the depression at six separate locations, some of which (51, 52, 53, 54, and 55) are part of the capillary flow unit 50, while the remaining location will result in the formation of the larger initiation capillary 30 and reaction chamber 40 when plates 12 and 14 are welded together.

EXAMPLES

The following examples are provided by way of illustration and explanation and as such are not to be viewed as limiting the scope of the present invention.

Example 1

Investigation of Sensitivity of CoaguChek™ Pro ACT Measurement to Heparin Concentration Example 1 was carried out according to the most preferred embodiment of the present invention. In particular, Table 2 lists the levels of the various components in the CoaguChek™ Pro ACT reagent applied to test cartridges like those described above. The cartridges were produced for use with the CoaguChek™ Pro monitors described above.

TABLE 2

Reagent Formulation

Reagent used in first clinic

| Level[1] (g/dL) | Component | Supplier (Catalog #) |
|---|---|---|
| 4.0 | Glycine | Mallinckrodt (5104) |
| 0.01 | Triton X-100 | Sigma (X100) |
| 1.0 | Gelatin | American Gelatin Co. (low bloom) |
| 1.0 | BSA | Sigma (A7030) |
| 5.0 | Sucrose | Sigma (S9378) |
| 0.02 | Sulfarhodamine B | Aldrich (23016,2) |
| 0.30 | Sulfatide | 0.8% sulfatide solution |
| 100 ng/mL rHTF | | Serbio (77800) |

[1]concentration in reconstituted reagent applied to APTT-format cartridges

Precision studies with these cartridges on both CoaguChek™ Pro and Plus monitors are shown in Table 3. Blood controls as well as heparinized blood aliquots were used in these studies. The assay results displayed by both sets of monitors were the actual times detected for clot formation.

TABLE 3

Precision Study
Production lot of CoaguChek ™ Pro ACT cartridges
Six monitors assaying each sample in triplicate
Raw clot times

| | Pro Monitors | | | Plus Monitors | | |
|---|---|---|---|---|---|---|
| | Mean | S.D. | C.V. | Mean | S.D. | C.V. |
| A. Blood aliquots with varying heparin levels (N = 18) | | | | | | |
| Blood Heparin Level (U/mL) | | | | | | |
| 0 | 24.7 | 0.7 | 2.8 | 23.5 | 0.6 | 2.5 |
| 1.5 | 80.9 | 4.0 | 5.0 | 78.8 | 3.3 | 4.1 |
| 3.0 | 220.3 | 23.3 | 10.6 | 246.6 | 30.1 | 12.2 |
| B. Blood Controls (N = 18) | | | | | | |
| Controls | | | | | | |
| APTT Level 1 | 24.8 | 0.6 | 2.5 | 23.9 | 0.9 | 3.7 |
| ACT #1 | 64.5 | 5.1 | 8.0 | 65.4 | 6.8 | 10.4 |
| ACT #1 + #2 | 155.9 | 15.1 | 9.7 | 142.1 | 10.0 | 7.0 |

Example 2

Effect of Sample Temperature on CoaguChek™ Pro ACT Assay

Figure 4A:
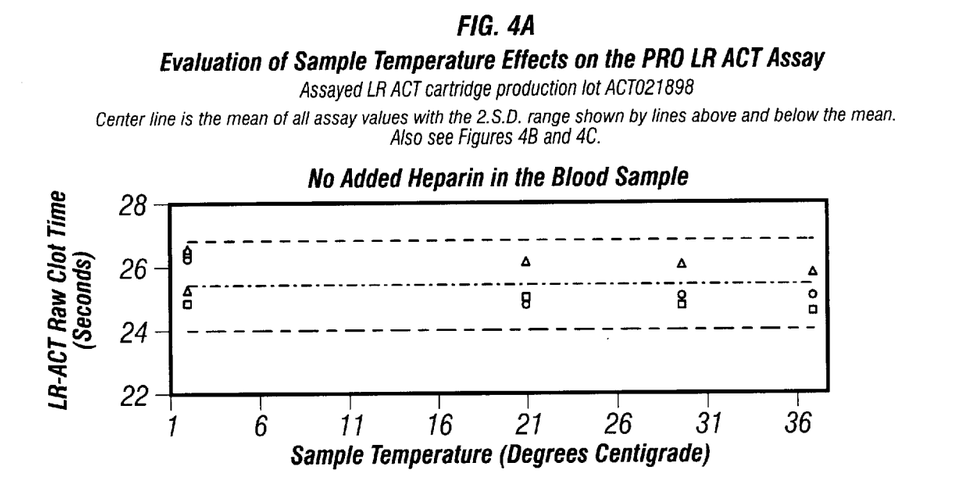
FIGS. 4A–4C shows the graphs generated in an evaluation of sample temperature effects on the method of the present invention.
Figure 4B:
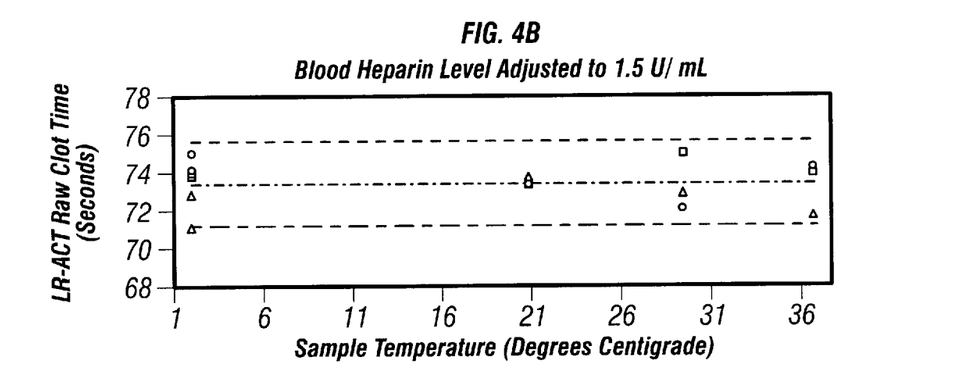
Figure 4C:
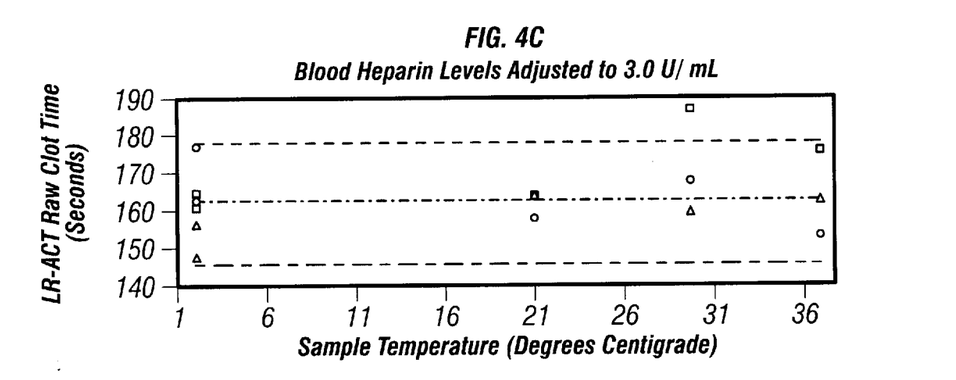

An evaluation of sample temperature effects on the CoaguChek™ Pro ACT assay was performed and the results shown in FIGS. 4A–C. While the specification is set at 12° to 32° C., the evaluation demonstrated no effect on performance of the CoaguChek™ Pro ACT cartridges in a temperature range from 2° to 37° C.

Example 3

Effect of Aprotinin on CoaguChek™ Pro ACT Assay

Another study evaluated the effect of aprotinin on the CoaguChek™ Pro ACT assay. While aprotinin is of greater concern for situations requiring the full range ACT assay (out to 6 U/mL), the known potency of aprotinin on the conventional celite-ACT assay requires an ACT assay to be evaluated for aprotinin affects. Table 4 contains the results of the evaluation—the aprotinin levels used in the relevant surgical procedures are below 200 KIU/mL and this study used a level of 500 KIU/mL which is significantly beyond the level expected in a surgical situation.

TABLE 4

Affect of Aprotinin on ACT Assays
Samples "A" had no added aprotinin, Samples "B" had aprotinin at a level of 500 KIU/mL

| Blood Heparin Levels (U/mL) | Sample | Mean secs. |
| --- | --- | --- |
| 1.0 | 1A | 53.7 |
| 1.0 | 1B | 54.1 |
| 2.0 | 2A | 101.7 |
| 2.0 | 2B | 109.1 |
| 3.0 | 3A | 191.8 |
| 3.0 | 3B | 227.2 |

Example 4

Effect of Hematocrit on CoaguChek™ Pro ACT Assay

Table 5 shows the results of studies to determine if hematocrit variations will affect the CoaguChek™ Pro ACT assay. The adjusted low and high hematocrit samples gave assay results within the specifications set with the unadjusted (normal) hematocrit samples. Therefore, hematocrit levels have not been found to influence CoaguChek™ Pro ACT results.

TABLE 5

A. CoaguChek ™ Plus hematocrit study with CoaguChek ™ Pro ACT (R&D lot)
Low and high hematocrit heparinized blood samples assayed in duplicate; unadjusted hematocrit (normal) heparinized blood samples assayed in quadruplicate

| Sample (HCT) | | mean seconds | Specification 80% to 120% of Mean Normal |
| --- | --- | --- | --- |
| Donor #1 | Low (25%) | 86.8 | |
| (1.5 U/mL) | Normal (44%) | 93.4 | 74.7 to 112.0 |
| | High (56%) | 107.6 | |
| Donor #2 | Low (21%) | 86.6 | |
| (2.0 U/mL) | Normal (42%) | 88.0 | 70.4 to 105.8 |
| | High (54%) | 88.1 | |
| Donor #3 | Low (21.5%) | 72.0 | |
| (2.0 U/mL) | Normal (44%) | 85.4 | 68.3 to 102.5 |
| | High (55%) | 90.6 | |
| Donor #4 | Low (23.5%) | 63.3 | |
| (1.5 U/mL) | Normal (46%) | 71.3 | 57.0 to 85.6 |
| | High (63%) | 82.2 | |
| Donor #5 | Low (22%) | 88.4 | |
| (2.0 U/mL) | Normal (41%) | 105.9 | 84.7 to 127.1 |
| | High (55%) | 122.6 | |

B. CoaguChek ™ Pro hematocrit study with CoaguChek ™ Pro ACT (Production lot ACT021898)
All samples assayed on three monitors three times
Blood heparin level adjusted to 1.5 U/mL

| | Low | Normal | High | Specification: 80% to 120% of Mean Normal |
| --- | --- | --- | --- | --- |
| Mean: | 88.6 | 84.5 | 100.3 | 67.6 to 101.4 |
| S.D.: | 6.6 | 1.3 | 5.5 | |
| C.V.: | 7.5 | 1.6 | 5.4 | |
| Hematocrit: | 21% | 43.5% | 55% | |

Example 5

Testing of Assay Sensitivity at Higher Dosing Levels

The protocol of Example 1 was followed, except that samples containing up to 6 U/mL heparin and higher were tested. It was surprisingly discovered that, in addition to its usefulness for determining the effectiveness of low to moderate heparin dosing, the present invention may also be used to determine the effectiveness of HR heparin dosing up to about 6 U/mL.

Example 6

Testing of Alternative Co-Factor Compositions

The protocol of Example 1 was followed, except that a phosphatide was used in place of a sulfatide, or mixed with a sulfatide. The combined weight of the sulfatide and the phosphatide was maintained at the same level as if the sulfatide was present alone (i.e., an equal weight of the sulfatide was subtracted for the amount of the phosphatide added). Varying ratios by weight of the phosphatide to the sulfatide were utilized in reagent compositions with TF. At moderate to high heparin levels of about 2 U/mL up to about 6 U/mL, compositions containing a phosphatide in place of a sulfatide, or a combination of a sulfatide and a phosphatide were found to have about equal effectiveness and sensitivity. For low range heparin dosing of about 0 to about 2 U/mL, it is preferred to use either a sulfatide alone, or a phosphatide and a sulfatide combination at between about 1/3 to about 3/1 ratio by weight.

While preferred and exemplary embodiments of the present invention have been described, the present invention may be practiced other than as specifically described herein and still fall within the scope of the present invention as set forth in the following claims.

What is claimed is:

1. A method for the determination of the clotting time of a blood sample, comprising contacting a blood sample with an effective amount of tissue factor and a sulfatide, and measuring the time by which a pre-determined degree of clotting is observed, wherein the blood sample is from a patient receiving heparin treatment, and the clotting time is used to determine the effectiveness of said treatment.

2. The method of claim 1, wherein the patient has received low to moderate heparin doses.

3. The method of claim 1, wherein the patient has received moderate to high heparin doses.

4. The method of claim 1, wherein heparin is present in the blood sample at between about 0 and about 3 U/ml.

5. The method of claim 1, wherein heparin is present in the blood sample at between about 3 U/mL and about 6 U/ml.

6. The method of claim 1, wherein said tissue factor is recombinant human tissue factor.

7. The method of claim 1, wherein said sulfatide is bovine brain sulfatide.

8. The method of claim 1, wherein said tissue factor is present in sufficient quantity in a reagent so that when an effective amount of said reagent is contacted with a blood sample to clot the sample, said sample comprises between about 50 and about 1000 ng/mL tissue factor.

9. The method of claim 8, wherein said sample after contact with said reagent comprises about 100 ng/mL tissue factor.

10. The method of claim 1, wherein said sulfatide is present in sufficient quantity in a reagent so that when an effective amount of said reagent is added to a blood sample to clot the sample, said sample comprises between about 1 and about 4 mg/mL sulfatide.

11. The method of claim 10, wherein said sample after contact with said reagent comprises about 3 mg/mL sulfatide.

12. The method of claim 1, wherein said tissue factor and said sulfatide are combined in a reagent prior to contacting the sample.

13. The method of claim 12, wherein said reagent further comprises a buffer and a stabilizer.

14. A method for the determination of the effectiveness of heparin treatment in a patient receiving same, comprising contacting a blood sample from a patient receiving heparin treatment with an effective amount of tissue factor and at least one co-factor selected from the group consisting of a sulfatide and a phosphatide, and measuring the time by which a pre-determined degree of clotting is observed, and relating said clotting time to heparin treatment effectiveness.

15. The method of claim 14, wherein the patient has received low to moderate heparin doses.

16. The method of claim 14, wherein the patient has received moderate to high heparin doses.

17. The method of claim 14, wherein heparin is present in the blood sample at between about 0 and about 3 U/mL.

18. The method of claim 14, wherein heparin is present in the blood sample at between about 3 U/mL and about 6 U/mL.

19. The method of claim 14, wherein said tissue factor is recombinant human tissue factor.

20. The method of claim 14, wherein said phosphatide is phosphatidyl choline.

21. The method of claim 14, wherein, when an effective amount of said tissue factor is added to a blood sample to clot the sample, said sample comprises between about 50 and about 1000 ng/mL tissue factor.

22. The method of claim 21, wherein said sample after contact with said effective amount of said tissue factor comprises about 100 ng/mL tissue factor.

23. The method of claim 14, wherein at least one of said phosphatide and said sulfatide are present in sufficient quantity in a reagent so that when an effective amount of said reagent is added to a blood sample to clot the sample, the sample comprises a combined total amount of said phosphatide and said sulfatide between about 1 and about 4 mg/mL.

24. The method of claim 23, wherein said blood sample after contact with said effective amount of said reagent comprises a combined total amount of said phosphatide and said sulfatide of about 3 mg/mL.

25. The method of claim 23, wherein said tissue factor and said at least one co-factor selected from the group consisting of a phosphatide and a sulfatide are combined in a reagent prior to contacting the sample.

26. The method of claim 25, wherein said reagent further comprises a buffer and a stabilizer.

* * * * *